United States Patent [19]

Okabe et al.

[11] Patent Number: 4,872,347

[45] Date of Patent: Oct. 10, 1989

[54] AUTOMATED ULTRASONIC EXAMINATION SYSTEM FOR HEAT TRANSFER TUBES IN A BOILER

[75] Inventors: Yoshimi Okabe, Tokyo; Keiichi Iwamoto, Nagasaki; Masaaki Torichigai, Nagasaki; Shozo Kaneko, Nagasaki; Joji Ichinari, Nagasaki; Kiyoshi Koizumi, Tokyo, all of Japan

[73] Assignees: Tokyo Electric Power Co.; Mitsubishi Jukogyo Kabushiki Kaisha, both of Tokyo, Japan

[21] Appl. No.: 151,093

[22] Filed: Feb. 1, 1988

[30] Foreign Application Priority Data

Jan. 30, 1987 [JP] Japan .................................. 62-19904

[51] Int. Cl.$^4$ ............................................. G01N 29/00
[52] U.S. Cl. ......................................... 73/634; 73/622
[58] Field of Search .............. 73/623, 622, 634, 866.5; 324/220, 221; 376/249, 252

[56] References Cited

U.S. PATENT DOCUMENTS

| | | | |
|---|---|---|---|
| 3,911,750 | 10/1975 | Prasher | 73/866.5 |
| 3,994,173 | 11/1976 | Ward et al. | 73/866.5 |
| 4,757,258 | 7/1988 | Kelly, Jr. et al. | 324/220 |

FOREIGN PATENT DOCUMENTS

| | | | |
|---|---|---|---|
| 5649957 | 5/1981 | Japan | 73/623 |
| 5794648 | 6/1982 | Japan | 73/634 |

*Primary Examiner*—Stewart J. Levy
*Assistant Examiner*—Louis M. Arana
*Attorney, Agent, or Firm*—Wenderoth, Lind & Ponack

[57] ABSTRACT

An automated ultrasonic examination system for heat transfer tubes in a boiler makes it possible to perform ultrsonic examination from inside of the heat transfer tubes without necessitating the removal of scale from the outer surfaces of the boiler tubes by polishing and without necessitating access to places where manual measurements are difficult or impossible to make. The system includes an insert tube adapted to be inserted into a cylindrical header to which one of the heat transfer tubes are connected, an insert tube moving device for moving the insert tube in the axial direction of the header and revolving it about its own axis, an ejection nozzle provided on the insert tube, a water pump for feeding pressurized water to the ejection nozzle, a cable adapted to be inserted from the ejection nozzle into the heat transfer tube as passed through the insert tube by the pressurized water fed from the water pump, a cable accommodation tank for accommodating the cable, a revolving submerged ultrasonic probe mounted at the tip end of the cable, and an ultrasonic examination unit for processing signals sent from the probe and displaying the results of examination. Preferably, a device for detecting a length of the cable inserted into the heat transfer tube is provided in the automated ultrasonic examination system.

6 Claims, 7 Drawing Sheets

AUTOMATED ULTRASONIC EXAMINATION SYSTEM FOR HEAT TRANSFER TUBES IN A BOILER

BACKGROUND OF THE INVENTION

1. Field of the Invention

The present invention relates to an automated ultrasonic examination system for heat transfer tubes in a boiler, that may be employed to conduct an ultrasonic examination of heater and reheater tubes in a boiler.

2. Description of the Prior Art:

Heretofore, when performing ultrasonic examination of heater tubes or reheater tubes in a boiler, as shown in FIG. 7 a worker entered a narrow space within a boiler, and after he had removed dust and scale adhering to surfaces of tubes 01, he performed ultrasonic examination from the outside of the tubes 01.

However, since the heater tubes or reheater tubes in a boiler are normally at a high location, in order to perform ultrasonic examination it is necessary to erect a scaffolding within the boiler. In addition, the heater tubes or reheater tubes are typically arranged in a dense array for enhancing thermal efficiency, and hence there are many narrow places where a worker cannot access the tubes. Furthermore, since the ultrasonic examination is performed from the outside, it is necessary to remove dust and scale deposited on the outer surfaces of the tubes, prior to examination. The present invention has been developed in light of the above-mentioned problems presented in the prior art.

SUMMARY OF THE INVENTION

It is therefore one object of the present invention to provide a novel automated ultrasonic examination system for heat transfer tubes in a boiler, which can perform ultrasonic examination from inside of the tubes, and which can easily conduct such as ultrasonic examination of tubes even when the tubes are at a high location or are plates so narrow that access to the tubes is difficult.

According to one feature of the present invention, there is provided an automated ultrasonic examination system for heat transfer tubes in a boiler, comprising an insert tube adapted to be inserted into a cylindrical body to which one ends of tubes to be examined are connected, an insert tube moving device for moving the insert tube in the axial direction of the cylindrical body and revolving the insert tube about its own axis, a pressurized water ejection nozzle provided on the insert tube, a pressurized water feed pump for feeding pressurized water to the pressurized water ejection nozzle, a cable adapted to be inserted from the pressurized water ejection nozzle into the tube to be examined as passed through the insert tube by the pressurized water fed from the pressurized water feed pump, a cable accommodation tank for accommodating the cable, a revolving submerged ultrasonic probe mounted at the tip end of the cable, and an ultrasonic examination unit for processing signals sent from the submerged ultrasonic probe and displaying the results of examination.

According to another feature of the present invention, there is provided the above-featured automated ultrasonic examination system which further comprises means for detecting a length of the cable inserted into the tube to be examined.

During the operation of the automated ultrasonic examination system for heat transfer tubes in a boiler according to the present invention, the insert tube is inserted into a header which is provided in association with a heater or a reheater in a boiler by making use of an inspection hole provided in an end wall of the header, the cable is inserted from the pressurized water ejection nozzle into the tube to be examined by the pressurized water fed from the pressurized water feed pump, and by means of the revolving submerged ultrasonic examination probe mounted at the tip end of the cable, ultrasonic examination is effected from inside of the tube.

With the automated ultrasonic examination system for heat transfer tubes in a boiler according to the present invention, the following advantages are attained:

(1) An ultrasonic examination probe can be easily inserted into a heat transfer tube by making use of an inspection hole in a header which is provided in a boiler, an insert tube and pressurized water, and hence, necessary examination can be achieved in a short period of time.

(2) Polishing of outer surfaces of tubes to be examined becomes unnecessary.

(3) Erection of a scaffolding is not necessary.

(4) Examination at places so narrow that access to the tubes is difficult becomes possible.

The above-mentioned and other objects, features and advantages of the present invention will become more apparent by referring to the following description of a preferred embodiment of the present invention taken in conjunction with the accompanying drawings.

DETAILED DESCRIPTION OF THE PREFERRED EMBODIMENT

One preferred embodiment of the present invention will be described referring to FIGS. 1 through 6.

Figure 1:
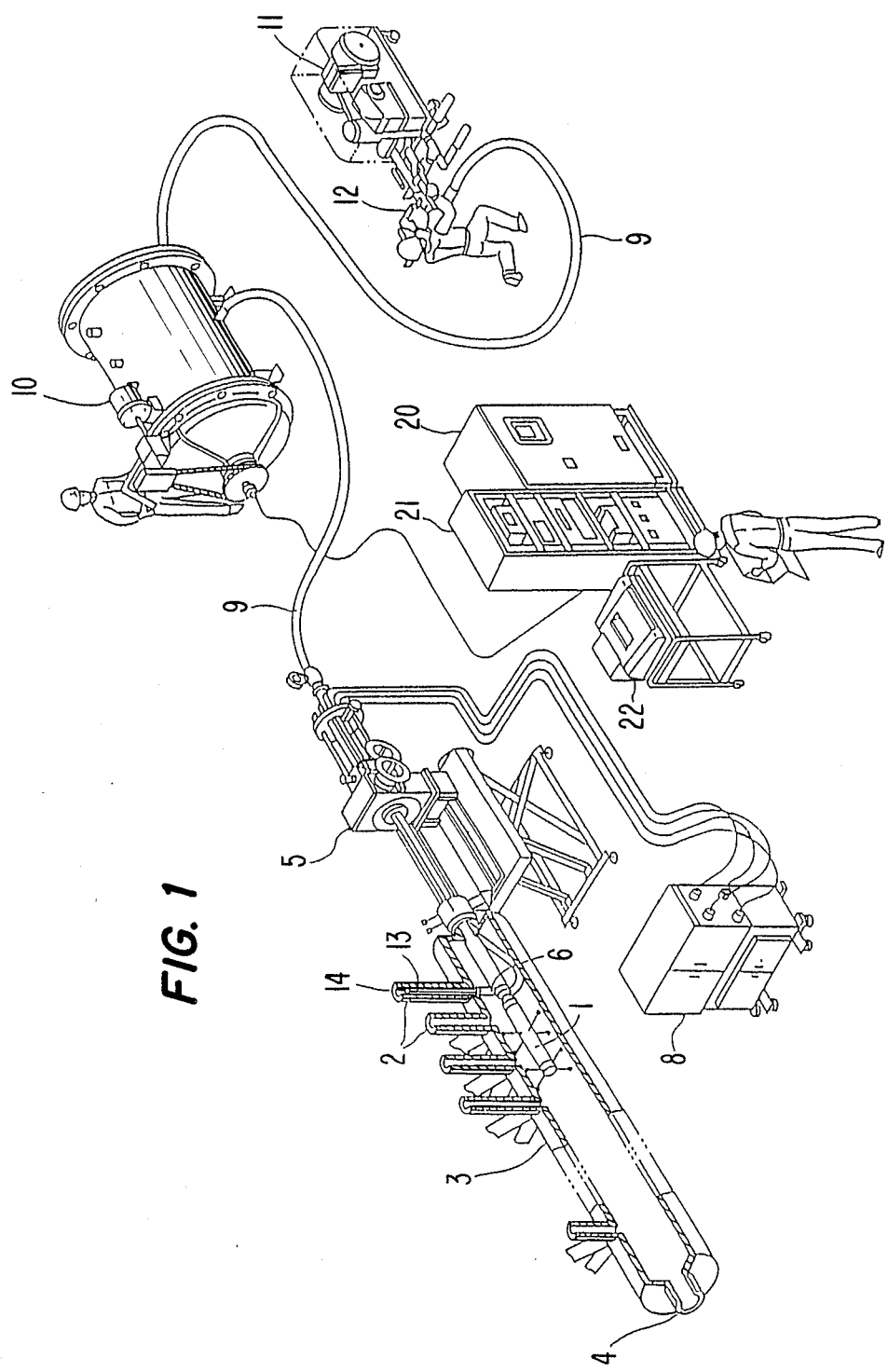
FIG. 1 is a perspective view showing a general layout of an automated ultrasonic examination system for heat transfer tubes in a boiler according to one preferred embodiment of the present invention.
Figure 2:
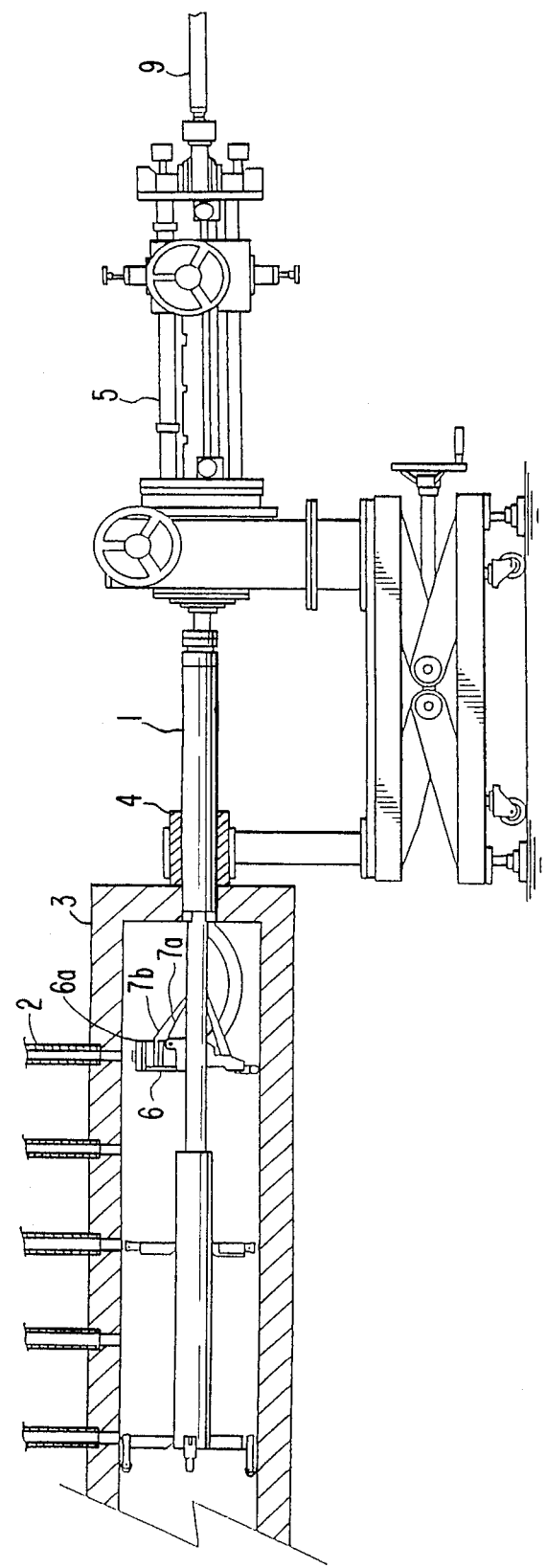
FIG. 2 is a front view partly in cross-section showing the state where an insert tube has been inserted into a header.
Figure 6:
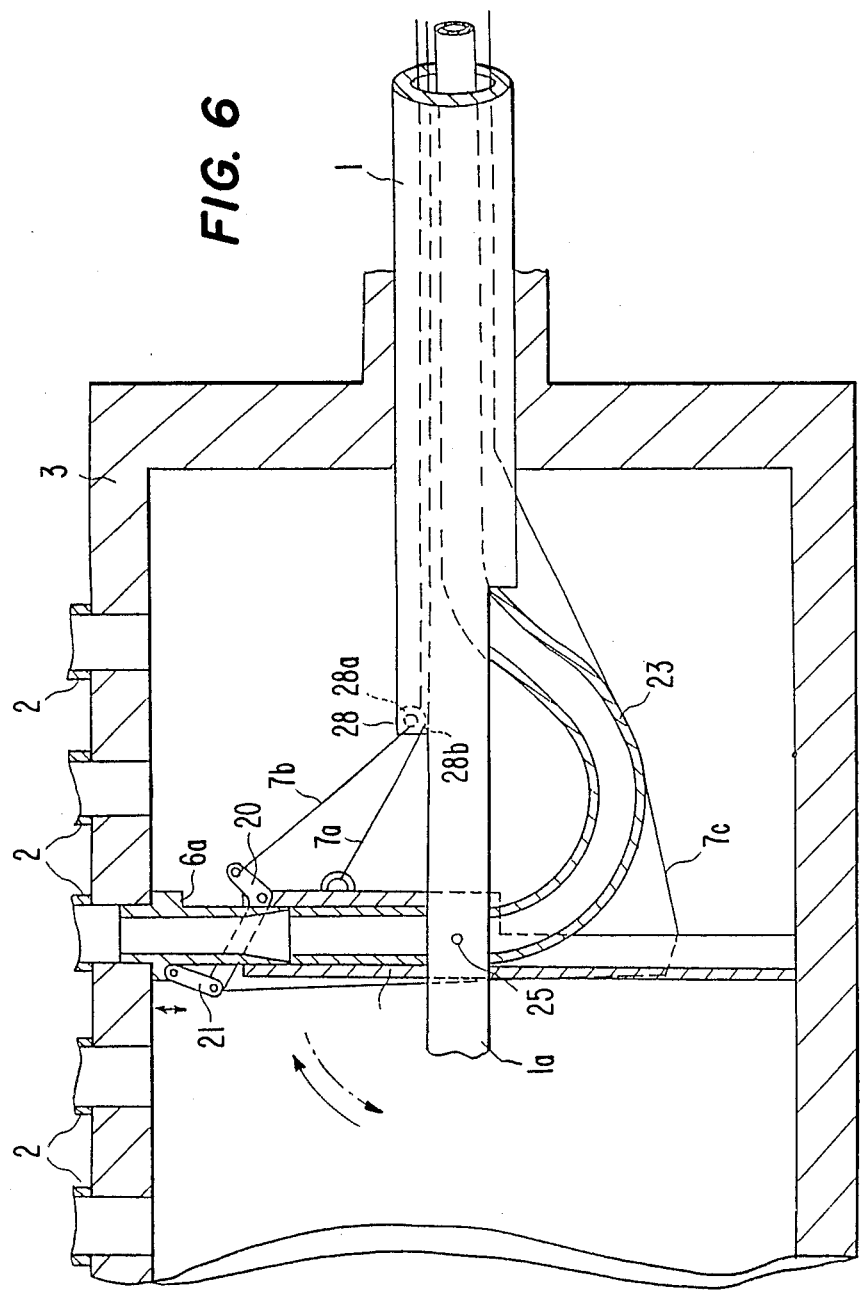
FIG. 6 is a detailed construction view partly in cross-section showing one example of an insert tube and a pressurized water ejection nozzle in an automated ultrasonic examination system according to the present invention.
Figure 7:
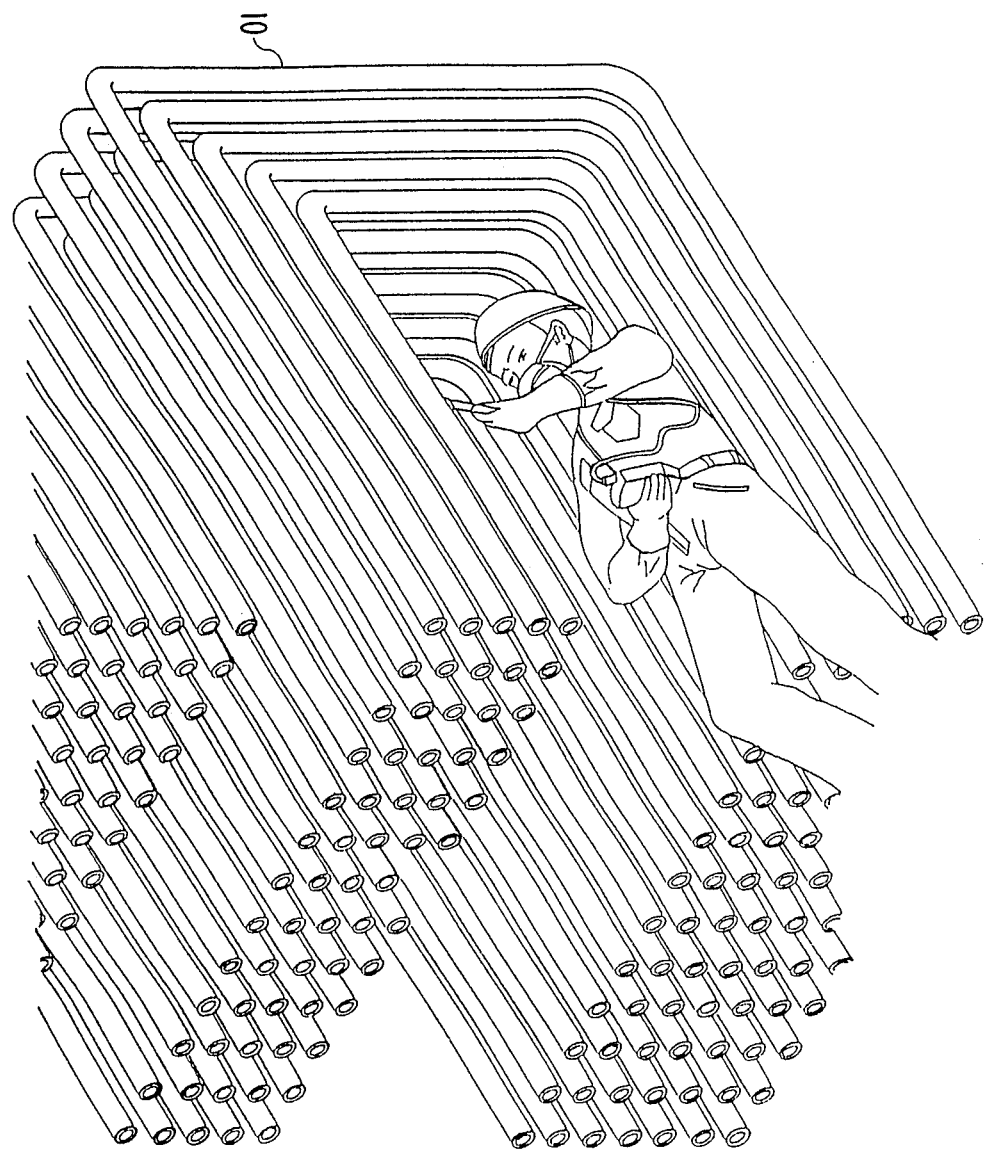
FIG. 7 is a perspective view showing a working condition of ultrasonic examination for heat transfer tubes in a boiler in the prior art.

At first, referring to FIG. 1 which shows a general layout of the automated ultrasonic examination system for heat transfer tubes in a boiler according to the present invention, reference numeral 1 designates an insert tube adapted to be inserted into a header (cylindrical body) 3 to which heating tubes (tubes to be examined) 2 are connected. This insert tube 1 is inserted through an inspection hole 4 provided in an wall of the header 3, and an insert tube moving device 5 for moving the insert tube 1 in the axial direction of the header 3 and revolving the insert tube 1 about its own axis, is disposed in the proximity of the inspection hole 4. The above-described insert tube 1 is generally formed by successively jointing a plurality of insert tube units each having a length of, for example, about 1 m, and is inserted into the header 3. As is best seen in FIG. 6, at the tip end portion of the foremost insert tube unit is pivotably mounted a pressurized water ejection nozzle 6. While this pressurized water ejection nozzle 6 is accommodated within the insert tube 1 when the insert tube 1 is inserted through the inspection hole 4, after the insert tube 1 has been inserted into the header 3, the pressurized water ejection nozzle 6 is erected at a right angle to the insert tube 1 by means of a wire 7a as shown in FIG. 2, so that a nozzle neck 6a at the tip end of the ejection nozzle 6 confronts an open end of the heater tube 2. And when another wire 7b is drawn, the above-mentioned nozzle neck 6a is extended from the tip end of the nozzle 6 to be pressed against the open end of the heater tube 2.

One example of the structure the above-described insert tube 1 and pressurized water ejection nozzle 6 will be described with reference to FIG. 6. The hollow insert tube 1 is provided with a forwardly opened portion at its front end, and at this portion are integrally formed support members 1a. The pressurized water ejection nozzle 6 is pivotably supported from these support members 1a by means of a support pin 25. A wire 7a and another wire 7c are connected to the pressurized water ejection nozzle 6 at different positions on the opposite sides of the support pin 25, and these wires are passed through the above-mentioned insert tube 1 and are respectively connected to a wire controller (not shown). By drawing the wire 7a by means of the wire controller, the pressurized water ejection nozzle 6 is rotated in the direction of the solid line arrow to a position extending perpendicular to the insert tube 1 as shown. However, by drawing the wire 7c, the pressurized water ejection nozzle 6 is rotated in the direction shown by the dash-dot line arrow and to a position extending parallel to the insert tube 1. In FIG. 6, reference numeral 28 designates a guide wheel, which is composed of a small guide wheel 28a and a large guide wheel 28b, and the above-mentioned wire 7a is wound around the large guide wheel 28b. To the pressurized water ejection nozzle 6 is mounted a nozzle neck 6a. This nozzle neck 6a rotates with the pressurized water ejection nozzle 6 when the latter is rotated via the wires 7a and 7c, and also may be extended towards the open end of the heater tube 2 by an L-shaped lever 20, a push-up lever 21 and a wire 7b so as to be pressed against the tube end opening. The above-mentioned wire 7b is wound around the small guide wheel 28a of the guide wheel 28, passes through the insert tube 1, and like the wires 7a and 7c, is connected to the wire controller. A hose 23 disposed within the insert tube 1 is connected to the nozzle neck 6a, and as shown in FIG. 6, this hose 23 extends through the pressurized water ejection nozzle 6 and is connected, on the opposite side, to a pressurized water feed hose 9 which will be described later. A provision is made for the introduction of pressurized water into this hose 23 and. A cable 13 (FIG. 3) having a revolving submerged ultrasonic probe at its tip end portion may be inserted into the heater tube 2 through the nozzle neck 6a by the action of the pressurized water as will be described later. It is to be noted that FIG. 6 illustrates merely one example of the insert tube 1 and the pressurized water ejection nozzle 6 and it is possible to employ different structures for these members. For instance, a modified structure in which the hose 23 is omitted and the insert tube 1 itself functions function as a hose, could be employed.

To the rear end of the above-described insert tube 1 is connected a pressurized water feed hose 9 to feed pressurized water to the above-described pressurized water feed nozzle 6 through a pressurized water passageway formed within the insert tube 1 (for instance, the hose 23 in the example shown in FIG. 6). The other end of this pressurized water feed hose 9 is connected to a delivery port of a pressurized water feed pump 11 via a cable accommodating apparatus 10, and at the delivery port of the pressurized water feed pump 11 is provided a pressurized water flow rate regulating and flow direction control device 12 for controlling the flow rate and direction of flow of pressurized water.

Figure 3:
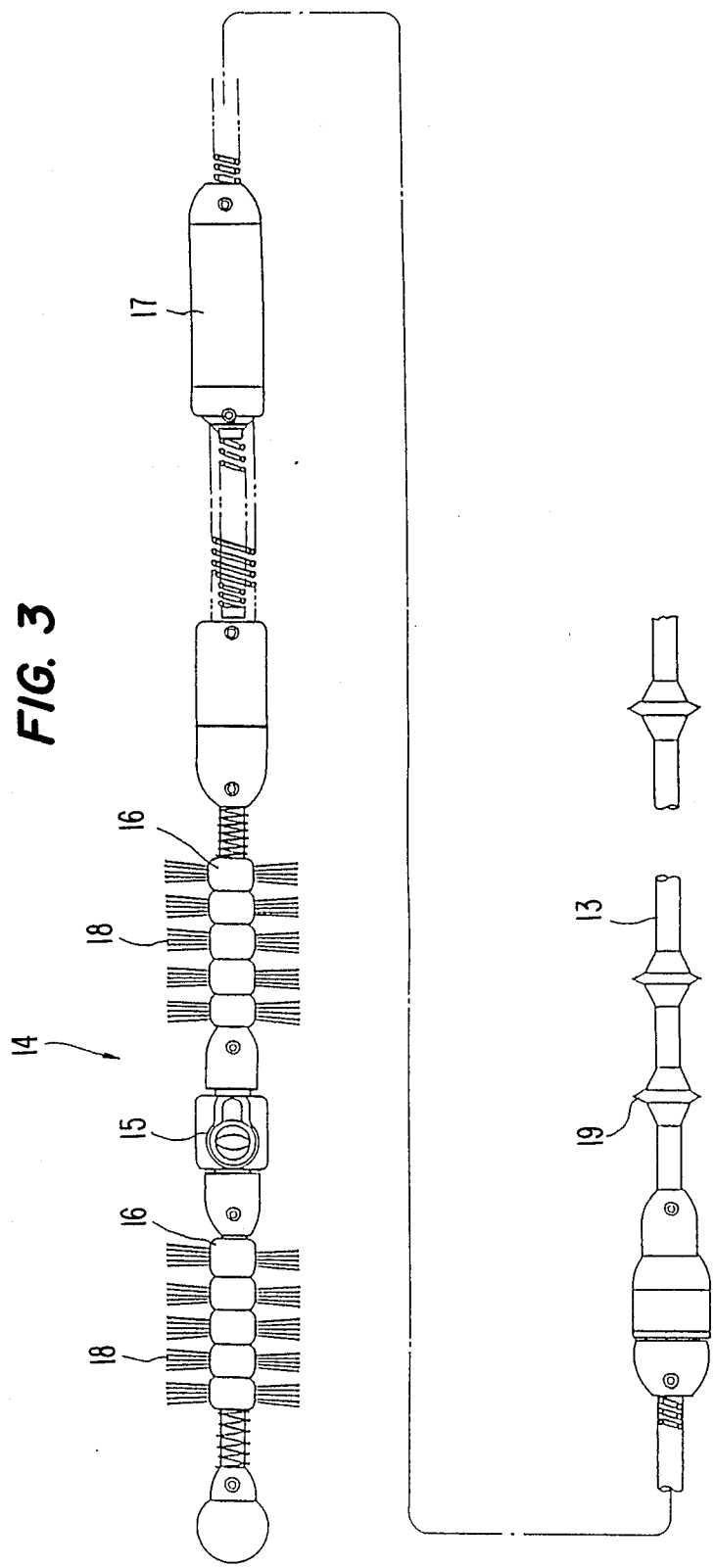
FIG. 3 is a front view showing a revolving submerged ultrasonic probe.
Figure 4:
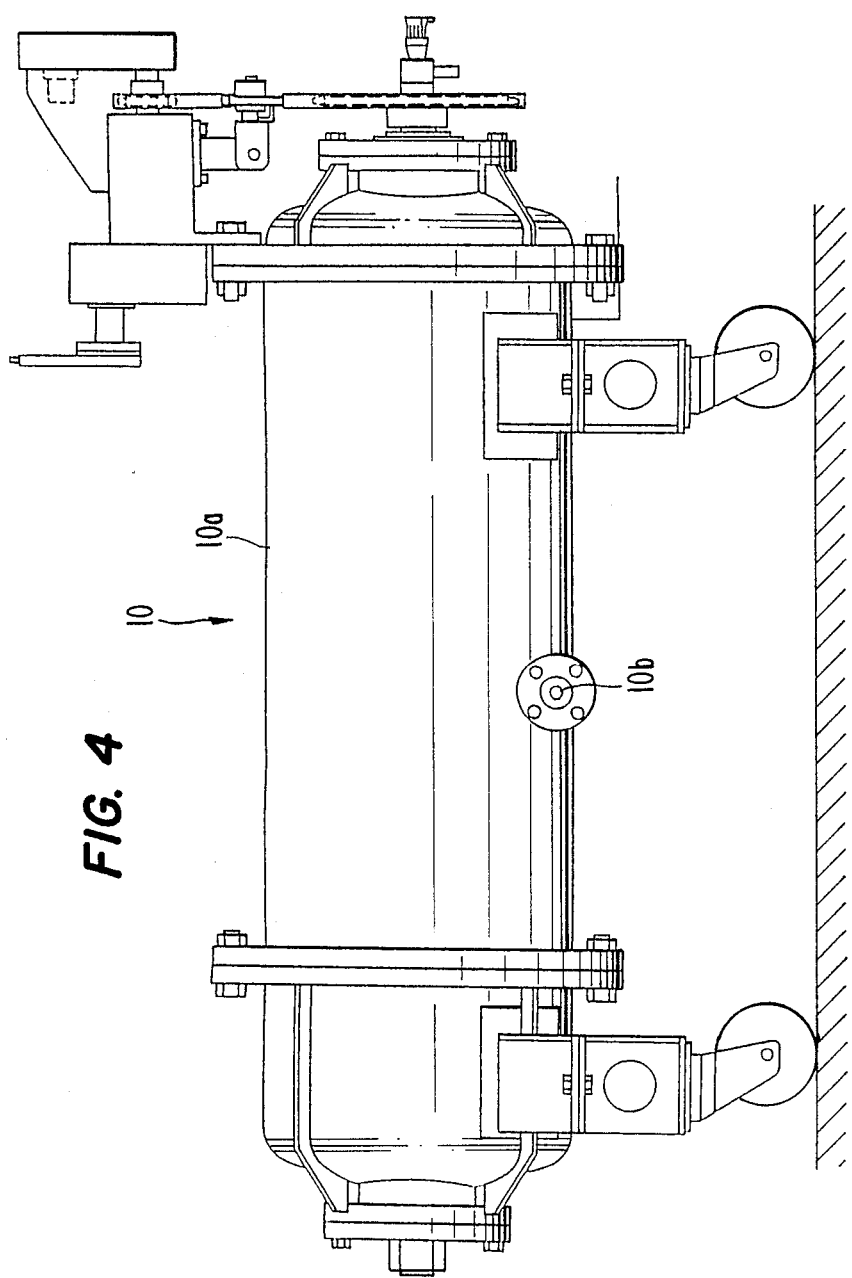
FIG. 4 is a front view showing a cable accommodating apparatus.

Within the above-mentioned cable accommodating apparatus 10 is accommodated a cable 13 shown in FIG. 3 as wound around a rotary drum (not shown). This cable 13 is flexible so that it may be conveyed by the pressurized water through the insert tube 1 and the pressurized water ejection nozzle 6 and into the heater tube 2. The rotary drum is disposed within a pressure tank 10a (See FIG. 4) of the cable accommodating apparatus 10, has an axis directed in the axial direction of the pressure tank 10a, and is either automatically rotated in accordance with the flow of the pressurized water or is manually rotated. In addition, the rotary drum is adapted to be moved in the axial direction of the pressure tank 10a by one pitch of cable winding for every revolution thereof so that the position of the cable 13 being paid out from the rotary drum or wound up therearound may always confront a cable pay-out/-wind-up port 10b provided at the center of the pressure tank 10a.

Furthermore, as shown in FIG. 3, at the tip end of the cable 13 is mounted a revolving submerged ultrasonic probe 14. This revolving submerged ultrasonic probe 14 includes a probe main body 15, centering jigs 16 for positioning the probe main body 15 on a center axis of the tube to be examined, and a motor 17 for rotating the probe main body 15. And in order for the same probe to be used in tubes having different diameters, the outer circumferential surfaces of the centering jigs 16 are studded with brushes 18 made of high molecular material. In addition, float members 19 are fixedly secured to the cable 13 at a fixed interval, and a propelling force for the cable 13 is generated by these float members. In FIG. 1, reference numeral 20 designates a cable insert length detector unit for detecting a rotational angle of the rotary drum in the cable accommodating apparatus 10 and calculating a feed length of the cable 13 on the basis of the rotational angle and the outer diameter of the rotary drum; and, reference numeral 21 designates an ultrasonic examination unit which processes signals sent from the revolving submerged ultrasonic probe 14 and outputting the results of examination to a printer 22 or the like display device.

Now, the measurement of a tube wall thickness of the heater tube 2 with the automated ultrasonic examination system according to the present invention having the above-described structure will be described.

At first, blind covers for the inspection holes 4,4 formed at the opposite ends of the header 3 are removed by them to form openings, and thereafter an insert tube moving device 5 is set in the proximity of an inspection hole 4. In the example shown in FIG. 5, insert tube moving devices 5 are set proximate the inspection holes 4 of the headers 3 on the inlet side as well as on the outlet side of the heater tubes 2.

After the insert tube 1 has been set on the insert tube moving device 5, a fiberscope is inserted into the insert tube 1 from the disconnected end until the tip end of the fiberscope arrives at the nozzle neck 6a of the pressurized water ejection nozzle 6. Under this condition, while an operator is looking into the fiberscope, the insert tube 1 is moved in the axial direction of the header 3 and revolved about its own axis by the insert tube moving device 5, so as to seek out the open end of a heater tube 2.

When the open end of the heater tube 2 has been found through the above-mentioned process, the fiberscope is withdrawn from the insert tube 1. At the header on one of the inlet side and the outlet side of the through which the cable is inserted (in FIG. 5, such a header is shown as inlet side header 3-1.), the insert tube 1 and the cable accommodating apparatus 10 are connected with each other by means of the hose 9, and also the cable accommodating apparatus 10 and the pressurized water feed pump 11 which is connected to the cable tank 32 are connected with each other by means of another hose 9.

Figure 5:
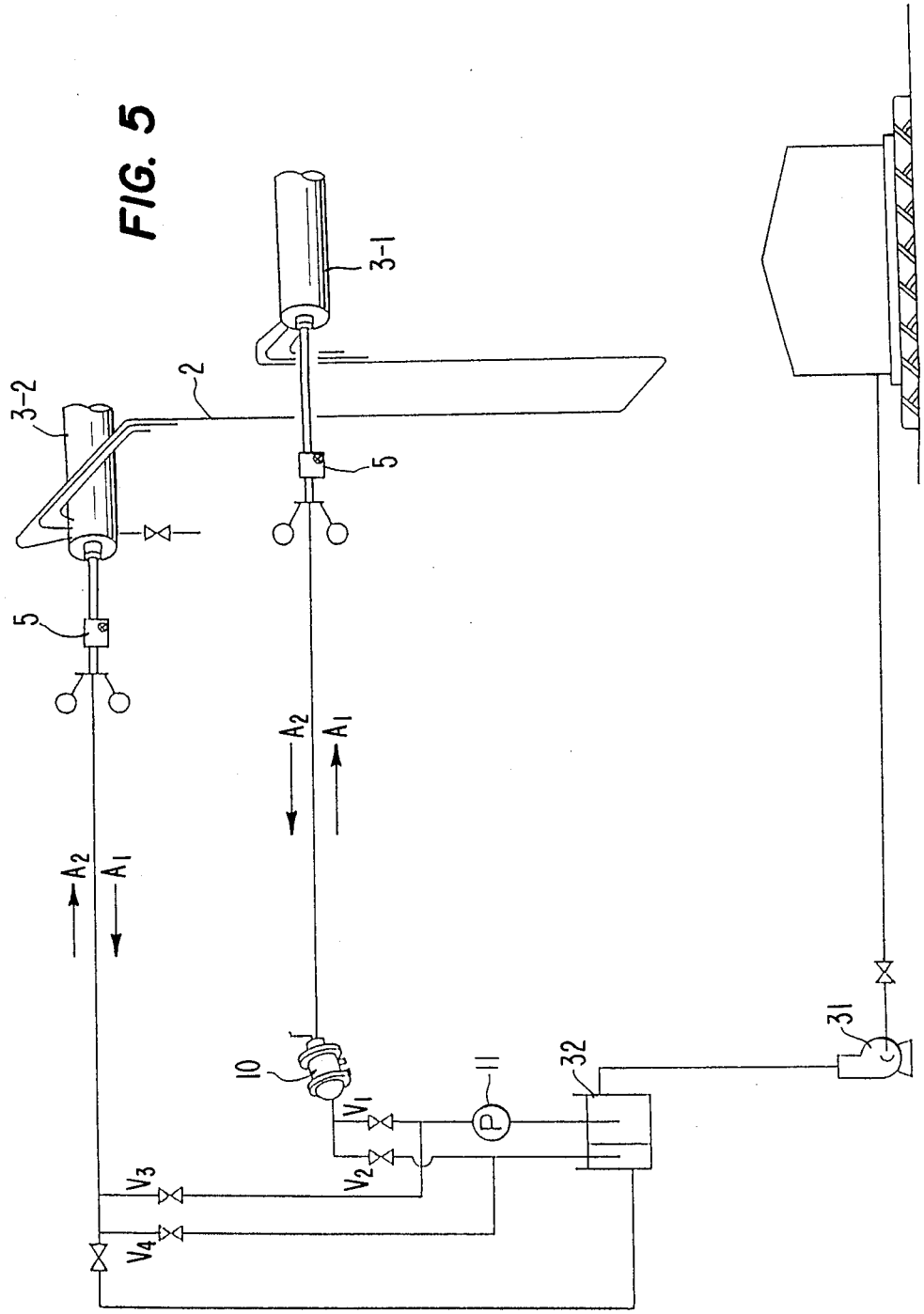
FIG. 5 is a piping diagram showing flows of pressurized water upon examination.

At another header on the other of the inlet side and the outlet side through which the cable is not inserted (in FIG. 5, such a header is shown as outlet side header 3-2), the insert tube 1 is directly connected with the pressurized water feed pump 11 by means of hose 9 without providing the cable accommodating apparatus. In these hoses 9, Valves $V_1$, $V_3$ are provided as shown in FIG. 5. The above cable accommodating apparatus 10 on the cable insertion side and the insert tube 1 on the other side are also connected to the cable tank 32 by means of hoses, to each of which Valve 2 or Valve 4 is provided, respectively.

In FIG. 5, numeral 31 shows a pump for feeding water from a water tank to cable tank 32.

In this state, the nozzle neck 6a of the pressurized water ejection nozzle 6 of the insert tube 1 in each of the inlet side and outlet side headers is pressed against the tube opening of the header tube 2 by drawing the wire 7b under the control of the wire controller 8.

Then, the Valves $V_1$ and $V_4$ are opened, the Valves $V_2$ and $V_3$ are closed, and the pressurized water feed pump 11 is started. The pressurized water flows as shown by arrow A, in FIG. 5 from the inlet side header 3-1 to the outlet side header 3-2, and the cable 13 is conveyed by the pressurized water through the insert tube 1 and the pressurized water ejection nozzle 6 into the heater tube 2. When a predetermined length of cable 13 is disposed in the heater tube 2, the pressurized water feed pump 11 is stopped and the Valves $V_1$, $V_2$ are closed so that the flow of the pressurized water is stopped.

Next, Valves $V_2$, $V_3$ are opened, Valves $V_1$, $V_4$ are kept closed, and the pressurized water feed pump 11 is started again. The pressurized water reversely flows from the outlet side header 3-2 to the inlet side header 3-1 as shown by arrow $A_2$ in FIG. 5, and the cable 13 moves in the heater tube toward the inlet side header 3-1, and is wound by the cable accommodating apparatus 10.

In the present invention, ultrasonic examination for the heater tube 2 is achieved from inside of the heater tube. The axial position of the probe can be detected by the cable insert length detector unit 20.

As described in detail above, according to the present invention, since ultrasonic examination can be performed from inside of tubes, the erection of scaffoldings and the removal of dust or scale deposited on the outside of the tubes is unnecessary, and ultrasonic examination can be easily conducted even at narrow places where a worker cannot access. According to experiments conducted by the inventors of the present invention, it was confirmed that a tube wall thickness of a heater tube having a total length of 40 m could be examined in about 3 minutes.

Since many changes and modifications can be made to the above-described structure and arrangement without departing from the spirit of the present invention, all matter contained in the above description and illustrated in the accompanying drawings shall be interpreted as being illustrative and not limitative of the invention

What is claimed is:

1. An automated ultrasonic examination system for examining heat transfer tubes open to a cylindrical body in a boiler, said system comprising:

an insert tube having a longitudinal axis;

an insert tube moving device for moving said insert tube axially and for rotating said insert tube about the longitudinal axis thereof;

a pressurized water ejection nozzle rotatably mounted to said insert tube about a pivot axis extending orthogonally to the axis of said insert tube;

a drive mechanism extending through said insert tube and operatively connected to said pressurized water ejection nozzle for rotating said nozzle about said pivot axis;

a pressurized water feed pump operatively connectable in the system to said pressurized water ejection nozzle for feeding pressurized water to said nozzle;

a cable insertable through said insert tube and said pressurized water ejection nozzle and payable from said nozzle under pressurized water fed to said nozzle;

a cable accommodation tank for accommodating said cable;

a revolvable and submergible ultrasonic probe mounted to an end of said cable for performing ultrasonic testing and for issuing signals indicative of the ultrasonic testing; and an ultrasonic examination unit operatively connectable in the system to said probe for processing the signals issued by said probe.

2. An automated ultrasonic examination system as claimed in claim 1, and further comprising detecting means for detecting the amount of cable paid out from said nozzle.

3. An automated ultrasonic examination system as claimed in claim 1, wherein said pressurized water ejection nozzle includes a base end portion mounted about said pivot axis to said insert tube and a tip end portion mounted to and extendable from said base end portion, and said drive mechanism is operatively connected to said tip end portion for extending said tip end portion from said base end portion.

4. An automated ultrasonic examination system as claimed in claim 1, wherein said ultrasonic examination unit includes a display device for displaying the processed signals.

5. An automated ultrasonic examination system as claimed in claim 1, wherein said nozzle is rotatable by said drive mechanism between a first position at which said nozzle generally extends along the longitudinal axis of said insert tube and a second position at which said nozzle extends orthogonally to said insert tube.

6. An automated ultrasonic system as claimed in claim 1, wherein said drive mechanism comprises wires connected to said nozzle.

* * * * *